US00PP36127P2

(12) United States Plant Patent
Boggan

(10) Patent No.: US PP36,127 P2
(45) Date of Patent: Sep. 17, 2024

(54) ***BEGONIA* PLANT NAMED 'Summer Storm'**

(50) Latin Name: *Begonia rex*
Varietal Denomination: Summer Storm

(71) Applicant: John Boggan, Washington, DC (US)

(72) Inventor: John Boggan, Washington, DC (US)

( * ) Notice: Subject to any disclaimer, the term of this patent is extended or adjusted under 35 U.S.C. 154(b) by 0 days.

(21) Appl. No.: 18/373,356

(22) Filed: Sep. 27, 2023

(51) Int. Cl.
*A01H 5/02* (2018.01)
*A01H 6/18* (2018.01)

(52) U.S. Cl.
USPC ..... Plt./343

(58) Field of Classification Search
USPC ..... Plt./343, 263.1
See application file for complete search history.

(56) References Cited

PUBLICATIONS

Gabriella Plants web site. citation for 'Summer Storm'. https://www.gabriellaplants.com/products/begonia-rex-summer-storm (Year: 2024).*

* cited by examiner

*Primary Examiner* — Karen M Redden
(74) *Attorney, Agent, or Firm* — Cassandra Bright

(57) ABSTRACT

A new and distinct cultivar of *Begonia* plant named 'Summer Storm' is disclosed, characterized by large, colorful, distinctively patterned leaves having a dark green background and distinct light yellow-green splotches. Plants are tolerant of heat and humidity and observed winter hardy to zone 7b without protection. Plant is robust, vigorous, easy to grow and easy to propagate, observed resistant to typical diseases and pests and not attractive to deer. The new cultivar is a *Begonia*, typically suited for garden and ornamental container use.

2 Drawing Sheets

Figure 1:
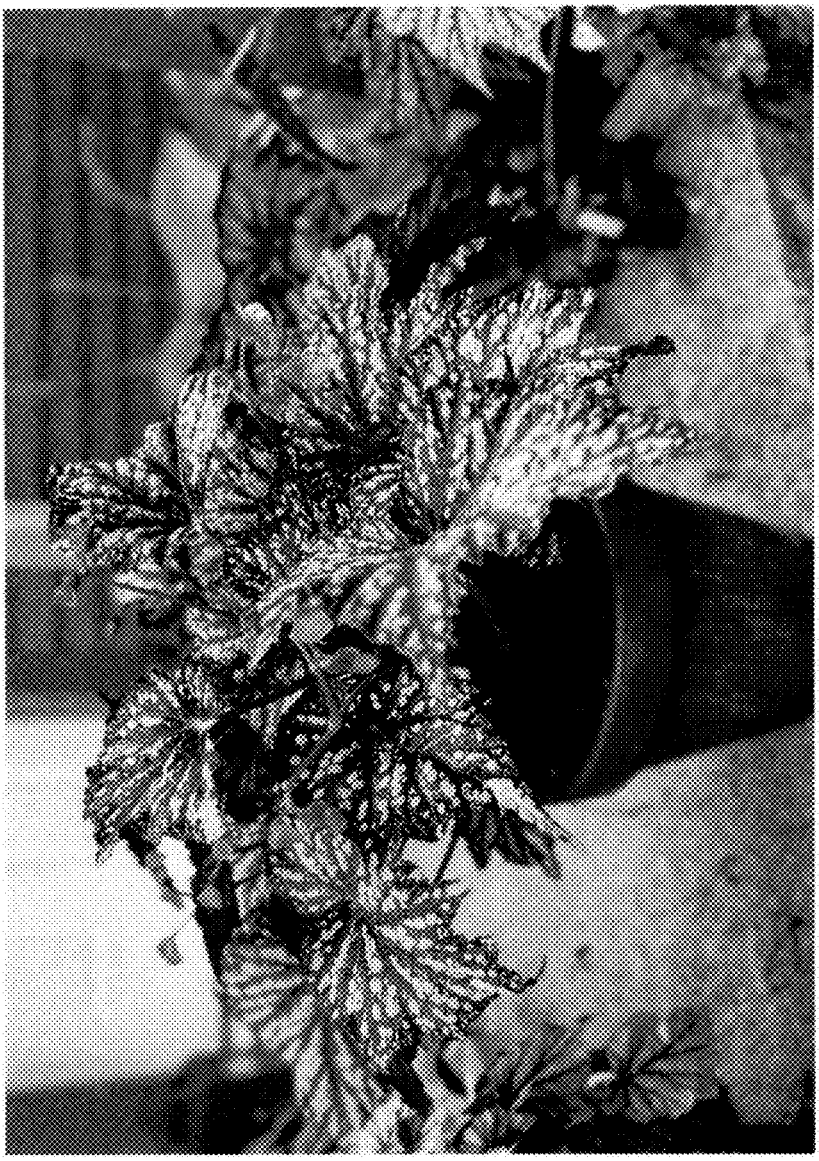

Latin name of the genus and species: *Begonia rex*.
Variety denomination: 'Summer Storm'.

BACKGROUND OF THE INVENTION

The new cultivar is a product of a planned breeding program. The new variety originated from the crossing of the seed parent, *Begonia rex* 'Taconite', unpatented, with the pollen parent, *Begonia rex* 'Eugene', unpatented, by the inventor during September of 2014. The crossing was made in Washington DC in the inventor's garden.

'Summer Storm' was selected by the inventor, in October of 2015 in Washington DC in the inventor's garden.

After selection of the new cultivar, asexual reproduction of 'Summer Storm' was first performed October of 2015 in Washington DC in the inventor's garden by leaf cuttings. 'Summer Storm' has since produced several generations and has shown that the unique features of this cultivar are stable and reproduced true to type.

SUMMARY OF THE INVENTION

The cultivar 'Summer Storm' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'Summer Storm.' These characteristics in combination distinguish 'Summer Storm' as a new and distinct *Begonia* cultivar:

1. Plant has large, colorful, distinctively patterned leaves having a dark green background and distinct light yellow-green splotches.

2. Plant is tolerant of heat and humidity.
3. Plant is observed winter hardy to zone 7b without protection.
4. Plant is robust, vigorous, easy to grow and easy to propagate.
5. Plant is resistant to pests (mealybugs such as *Planococcus citri*, scale *Saissetia coffeae*) and diseases (fungal diseases such as *Erysiphe, Botrytis cinerea* and bacterial leaf spot *Xanthomonas begonia*), and is not attractive to deer.

PARENTAL COMPARISON

Plants of the new cultivar 'Summer Storm' are similar to the seed parent in most horticultural characteristics. However, plants of 'Summer Storm' differ in the following:

1. The new variety is taller growing, with a more upright stem
2. The new variety has more deeply serrated leaves
3. The new variety has a distinct silver pattern on the leaf; 'Taconite' has a uniformly dark leaf with indistinct markings.

Plants of the new cultivar 'Summer Storm' are similar to the pollen parent in most horticultural characteristics. However, plants of 'Summer Storm' differ in the following:

1. The new variety is larger growing overall.
2. The new variety has bigger leaves.
3. The new variety has a more spreading growth habit.
4. The new variety has a more well-defined leaf pattern with fewer but larger, more distinct silver markings ('Eugene' has numerous, smaller silver markings that are less distinct).

COMMERCIAL COMPARISON

Plants of the new cultivar 'Summer Storm' are similar to the commercial variety 'Sterling Moon' U.S. Plant Pat. No.

33,164 in most horticultural characteristics. However, 'Summer Storm' differs in the following:

1. The new variety has foliage with a daker green background than this comparator.
2. The new variety is more tolerant of heat and humidity than this comparator.
3. The new variety is more root hardy than this comparator.
4. The new variety has a longer leaf size than this comparator.
5. Plants of the new variety grow about 50% wider than plants of this comparator.

Plants of the new cultivar 'Summer Storm' are similar to the commercial variety 'Fireworks', unpatented, in most horticultural characteristics. However, 'Summer Storm' differs in the following:

1. The new variety is more cold hardy than 'Fireworks'.
2. The new variety blooms more reliably and has a larger flower size than 'Fireworks'.
3. Plants of the new variety are taller and more upright than plants of 'Fireworks'.
4. The new variety has sturdier foliage which is less prone to damage (physical damage such as wind and rain) than 'Fireworks'.

BRIEF DESCRIPTION OF THE PHOTOGRAPHS

The accompanying photograph in FIG. 1 illustrates in full color a typical plant of 'Summer Storm' grown outdoors in West Newbury, Massachusetts. This plant is approximately 1 year old, in a 6 inch pot.

Figure 2:
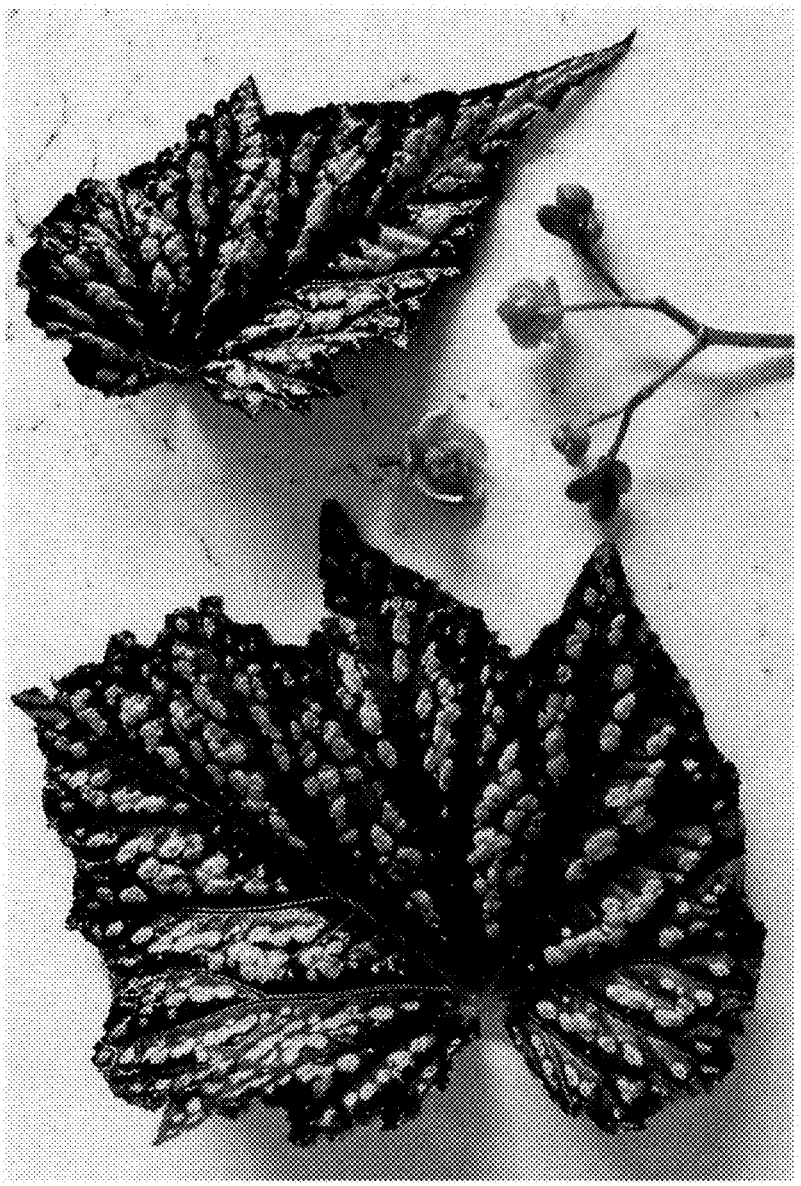

FIG. 2 illustrates a close-up view of the flowers and foliage.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'Summer Storm' plants grown in outdoors in West Newbury, Massachusetts during Spring. Temperatures ranged from about 15° C. to 35° C. during the day and about 15° C. to 26° C. at night. No artificial light, photoperiodic treatments or chemical treatments were given to the plants. Measurements and numerical values represent averages of typical plant types.

Botanical classification: *Begonia rex* 'Summer Storm'.

Age of the plant described: Approximately 3 years.

Container size of the plant described: 1-gallon commercial container.

PROPAGATION

Typically reproduced commercially by tissue culture. Leaf cutting propagation is also possible.

PLANT

Growth habit: Bushy, outwardly spreading flowering tender perennial.

Height: About 39 cm.

Plant spread: About 90 cm.

Growth rate: Moderate.

Branching characteristics:

*Quantity of branches*.—About 25.

*Characteristics of branches*.—Length: About 17 cm. Form: Round in cross section. Diameter: Approximately 0.5 cm to 1.0 cm. Color: Near RHS Greyed-Red 178A. Texture: Pubescent, moderately hirsute. Strength: Weak to moderate.

Internode length: Average 11 cm.

FOLIAGE

Arrangement: Emerging basally, with maturity 5 emerging from a branch split.

Quantity: Approximately 5 per branch.

Average length: Average range 21 cm.

Average width: Average range 16 cm.

Shape of blade: Rhomboid.

Apex: Acute.

Base: Peltate.

Margin: Hierarchically serrated.

Texture of top surface: Glabrous, leathery.

Texture of bottom surface: Hirsute, mainly along main veins.

Aspect: Puckered, overall flat.

Color:

*Young foliage upper side*.—RHS Yellow-Green 146C w Purple N77A overlay.

*Young foliage under side*.—RHS Red-Purple 59A with 145C splotches.

*Mature foliage upper side*.—RHS Yellow-Green 148A with Purple N77 overlay and margins and 145C spots.

*Mature foliage under side*.—RHS Green 138C with Greyed-Purple 187A splotches.

Venation:

*Type*.—Palmate.

*Venation color upper side*.—Near RHS Greyed-Purple N187C.

*Venation color under side*.—Near RHS Greyed-Purple N186C.

Petiole:

*Length*.—Average 24 cm.

*Diameter*.—Average 5 mm.

*Color*.—Near RHS Greyed-Purple 183A.

*Texture*.—Mainly smooth with infrequent pubescence.

Stipule description: 1 or 2 per node, non-fleshy, becoming completely dry and papery before leaves fully expand.

*Length*.—Approximately 1 cm.

*Diameter*.—Approximately 0.5 cm.

*Color*.—RHS Greyed-Orange 174A with 177C highlights.

*Texture*.—Glabrous.

FLOWER

Flowering habit: Continuously flowering during Summer. Flowering begins after about 100 days from a rooted cutting.

Inflorescence and flower type and habit: Single flowers arranged in axillary cymes. Cymes held slightly above or within foliage, approximately 2 to 4 flowers per cyme.

Cyme size:

*Diameter*.—Approximately 9 to 12 cm.

*Height*.—Approximately 4.5 cm.

Flowers per inflorescence: Average 5 to 8.

Flower longevity on plant: About 10 days, depending upon environmental conditions.
Persistent or self-cleaning: Self-Cleaning.
Bud:
*Shape*.—Ovate.
*Length*.—Approximately 1.5 cm.
*Diameter*.—Approximately 1.0 cm.
*Color*.—Near Greyed-Purple 185C.
Flower size:
*Diameter*.—Approximately 3.0 cm.
*Depth*.—Approximately 1 cm.
Female flower tepals:
*Quantity*.—4 or 5.
*Arrangement*.—Rotate overlapping.
*Length*.—Approximately 1.9 cm.
*Width*.—Approximately 1.5 cm.
*Shape*.—Ovate.
*Apex*.—Acute.
*Base*.—Truncate.
*Margin*.—Entire.
*Aspect*.—Slight upward curve.
*Texture, upper and lower surfaces*.—Glabrous.
*Appearance, upper and lower surfaces*.—Slightly iridescent.
*Color*.—When opening, upper surface: Near RHS Red 50A. When opening, lower surface: Near RHS Red 50C. Fully opened, upper surface: Near RHS Red 55C; 55A margins. Fully opened, lower surface: Near RHS Red 55B; 55A margins.
Flower bracts:
*Quantity per flower*.—1 to 2 per node.
*Shape*.—Ovate.
*Length*.—Approximately 3 cm.
*Diameter*.—Approximately 1.5 cm.
*Apex*.—Acute.
*Base*.—Truncate.
*Margin*.—Entire.
*Texture*.—Glabrous.
*Color*.—Near RHS Greyed-Purple 185A turning 186D.
Male flower tepals:
*Quantity*.—2.
*Length*.—1.4 cm.
*Width*.—1 cm.
*Shape*.—Oval.
*Apex*.—Acute.
*Base*.—Obtuse.
*Margin*.—Entire.
*Color*.—RHS Red 39B upper and lower surfaces.
Peduncles:
*Length*.—Average 5 cm.
*Diameter*.—Approximately 5 mm.
*Angle*.—About 35° to the lateral branch.
*Strength*.—Strong.
*Texture*.—Glabrous.
*Color*.—Near RHS Red 42A.
Pedicels:
*Length*.—Average 2.5 cm.
*Diameter*.—Approximately 2 mm.
*Angle*.—About 45° to the lateral branch.
*Strength*.—Strong.
*Texture*.—Glabrous.
*Color*.—Near RHS Red 42A.
Fragrance: None.

REPRODUCTIVE ORGANS

Stamens:
*Number*.—135, arising from staminoidal column.
Anthers:
*Description*.—Oblong fan.
*Length*.—Free portion about 2 mm.
*Color*.—Near RHS Yellow 11A.
*Pollen*.—Scant. Near RHS Yellow 10A.
Pistil:
*Number*.—4.
*Length*.—Approximately 0.5 cm.
*Style*.—Length: Approximately 3 mm. Color: Near RHS Colored near Greyed-Orange 167A.
*Stigma*.—Shape: Undulating fan. Color: Near RHS Colored near 168A. Ovary Color: Near RHS Greyed-Red 182A.

OTHER CHARACTERISTICS

Seeds and fruits: Female flower produces a capsule with 3 unequal wings.
*Size*.—2.4 cm long, 1 cm tall, 1.5 cm wide at widest point.
*Color*.—RHS 179A with 183A highlights.
Disease/pest resistance: Observed less susceptible to common diseases (fungal diseases such as *Erysiphe, Botrytis cinerea* and bacterial leaf spot *Xanthomonas begonia*) and pests (mealybugs such as *Planococcus citri*, scale *Saissetia coffeae*) of *Begonia* have been observed in the new variety.
Temperature tolerance: USDA Zone 7b-9. Observed to survive Winter temperature of −12° C. in the ground and −1° C. in a pot outdoors.

What is claimed is:

1. A new and distinct cultivar of *Begonia* plant named 'Summer Storm' as herein illustrated and described.

* * * * *